United States Patent [19]

Engel et al.

[11] 4,353,919
[45] Oct. 12, 1982

[54] ANALGESIC AND ANTIPYRETIC PHARMACEUTICAL COMPOSITIONS CONTAINING A BENZOTHIAZOL-2(3H)-ONE

[75] Inventors: Wolfhard Engel, Biberach; Günter Trummlitz, Warthausen; Wolfgang Eberlein, Biberach; Günther Schmidt, Biberach; Günther Engelhardt, Biberach; Rainer Zimmermann, Mittelbiberach, all of Fed. Rep. of Germany

[73] Assignee: Dr. Karl Thomae Gesellschaft mit beschränkter Haftung, Biberach, Fed. Rep. of Germany

[21] Appl. No.: 254,539

[22] Filed: Apr. 15, 1981

Related U.S. Application Data

[63] Continuation-in-part of Ser. No. 163,964, Jun. 30, 1980, abandoned.

[30] Foreign Application Priority Data

May 2, 1980 [DE] Fed. Rep. of Germany ....... 3016816
May 10, 1980 [DE] Fed. Rep. of Germany ....... 3017977

[51] Int. Cl.³ .......................................... A61K 31/425
[52] U.S. Cl. .................................................. 424/270
[58] Field of Search ....................................... 424/270

[56] References Cited

PUBLICATIONS

Chem. Abst. 87-84647y (1977).
Antonova et al., Mh. Chem., 107, 1487–1491, (1976).
Elderfield et al., J. Org. Chem., 18, 1092–1103, (1953).
Hunter et al., J. Chem. Soc., 1935, 1755–1761.
Mazzone et al., Il Farmaco, Ed. Sc. 32, 348–358, (1977).
Agoulezz et al., Chem. Abst., 81, 152 075p (1974).

*Primary Examiner*—Stanley J. Friedman
*Attorney, Agent, or Firm*—Hammond & Littell, Weissenberger & Muserlian

[57] ABSTRACT

Analgesic and antipyretic pharmaceutical dosage unit compositions containing as an active ingredient a compound of the formula

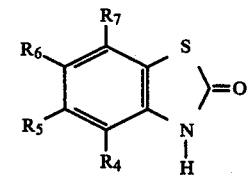

wherein
- $R_5$ is methyl or methoxy, and $R_4$, $R_6$ and $R_7$ are hydrogen; or
- $R_6$ is fluorine or chlorine, and $R_4$, $R_5$ and $R_7$ are hydrogen; or
- $R_7$ is chlorine, and $R_4$, $R_5$ and $R_6$ are hydrogen; or
- $R_5$ and $R_6$ are methoxy, and $R_4$ and $R_7$ are hydrogen; or
- $R_4$ is methyl or chlorine, and $R_5$, $R_6$ and $R_7$ are hydrogen;

and methods of using said compounds as analgesics and antipyretics.

4 Claims, No Drawings

ANALGESIC AND ANTIPYRETIC PHARMACEUTICAL COMPOSITIONS CONTAINING A BENZOTHIAZOL-2(3H)-ONE

This is a continuation-in-part application of copending application Ser. No. 163,964, filed June 30, 1980, now abandoned.

This invention relates to novel pharmaceutical compositions containing a known benzothiazol-2(3H)-one as an active ingredient, and to methods of using the same as analgesics and antipyretics.

More particularly, the present invention relates to analgesic and antipyretic pharmaceutical dosage unit compositions containing as an active ingredient a 4-, 5-, 6- or 7-monosubstituted or 5,6-disubstituted benzothiazol-2(3H)-one of the formula

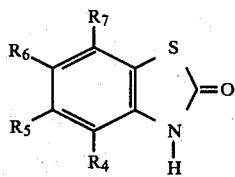

wherein
- $R_5$ is methyl or methoxy, and $R_4$, $R_6$ and $R_7$ are hydrogen; or
- $R_6$ is fluorine or chlorine, and $R_4$, $R_5$ and $R_7$ are hydrogen; or
- $R_7$ is chlorine, and $R_4$, $R_5$ and $R_6$ are hydrogen; or
- $R_5$ and $R_6$ are methoxy, and $R_4$ and $R_7$ are hydrogen; or
- $R_4$ is methyl or chlorine, and $R_5$, $R_6$ and $R_7$ are hydrogen;

and to methods of using said benzothiazolones as analgesics and antipyretics.

THE PRIOR ART

The compounds embraced by formula I above are disclosed in the following publications which deal exclusively with chemical or physical aspects of the compounds:

(a) D. Simov and A. Antanova, God. Sofii. Univ. Khim. Fak. 67, 287–293 (1972–1973; publ. 1976); C.A. 86, 154 756p (1977): This paper mentions among others 5-methoxy-2(3H)-benzothiazolone and 6-chloro-2-(3H)-benzothiazolone. Similar in content is the paper by A. Antanova and D. Simov, Mh. Chem. 107, 1487–1491 (1976);

(b) R. C. Elderfield and F. W. Short, J. Org. Chem. 18, 1092–1103 (1953). This paper discusses 7-chloro-2(3H)-benzothiazolone, among others;

(c) A. F. Aboulezz, S. M. A. Zayed, W. S. El-Hamouly and M. L. El-Sheikh, Egypt. J. Chem. 16, 355–359 (1973); C.A. 81, 152 075p (1974). This publication describes a method for the synthesis of 5,6-dimethoxy-2(3H)-benzothiazolone, among others;

(d) R. F. Hunter and E. R. Parken, J. Chem. Soc. 1935, 1755–1761: The compound 6-chloro-2(3H)-benzothiazolone is described.

(e) German Offenlegungsschrift 2,924,712 publ. Dec. 20, 1979;

(f) 6-fluoro-2(3H)-benzothiazolone and 6-chloro-2(3H)-benzothiazolone are described in a paper by G. Mazzone and G. Pappalardo, Il Farmaco, Ed. Sc. 32, 348–354 (1977), which deals with the synthesis of potential antimitotics;

(g) U.S. Pat. No. 3,812,138; and (h) Fiedländer 22/1, pg. 324 (1939); see also German Patent No. 615,131 to I. G. Farben-industrie A. G.

THE INVENTION

We have discovered that the compounds of the formula I exhibit effective analgesic and antipyretic properties.

The compounds of the formula I may be prepared by the following methods:

Method A

By reacting a 2-amino-thiophenol of the formula

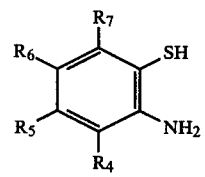

wherein $R_4$ to $R_7$ have the meanings previously defined with N,N'-carbonyl diimidazole in an anhydrous solvent such as benzene, toluene or other hydrocarbons, tetrahydrofuran, dioxane, or a similar cyclic ether, at temperatures up to the boiling point of the reaction mixture. In general, it is sufficient to remove the solvent in vacuo and to recrystallize the reaction product from, for example, 1,2-dichloroethane, ethanol, or methanol.

Method B

By hydrolyzing a benzothiazole of the formula

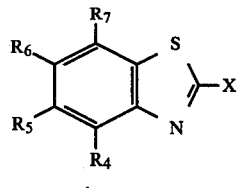

wherein
- $R_4$ to $R_7$ have the meanings previously defined, and
- X is chlorine, bromine or alkoxy of 1 to 3 carbon atoms, at temperatures between 0° and 120° C., preferably at the boiling point of the reaction mixture, by treatment with an aqueous mineral acid, for example with concentrated hydrochloric acid or hydrobromic acid, 20 to 60% sulfuric acid, or semi-concentrated phosphoric acid. The reaction can be carried out in the presence or absence of an inert, water-miscible solvent, such as methanol, ethanol, 1-propanol, 2-propanol, tetrahydrofuran, 1,4-dioxane or 1,2-ethandiol.

Method C

By cyclocondensing an o-nitrophenylthio-acetic acid of the formula

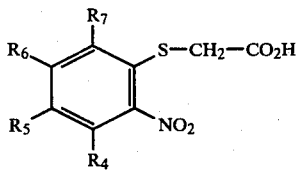

(IV)

wherein
R4 to R7 have the meanings previously defined, by heating the same, preferably to reflux temperature, with acetic acid anhydride to produce a 3-acetyl-benzothiazol-2(3H)-one intermediate of the formula

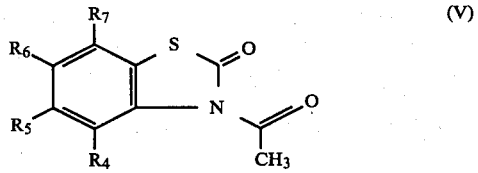

(V)

wherein R4 to R7 have the meanings previously defined.

The reaction is catalytically accelerated by the addition of an alkali metal acetate, such as sodium acetate, or a tertiary organic base, such as pyridine or triethylamine; however, it also proceeds in the absence of catalysts with the same yield.

The acetyl group of the intermediate of the formula V can be split off by reacting the compound in aqueous solution with an alkali metal or alkaline earth metal hydroxide, for example, with aqueous sodium, potassium or barium hydroxide; or with an aqueous amine or ammonium hydroxide solution, for example, with concentrated ammonia or a solution of benzyl trimethyl ammonium hydroxide; or by treating the intermediate with an aqueous mineral acid, such as concentrated hydrochloric acid or hydrobromic acid, semi-concentrated sulfuric or phosphoric acid, to form the corresponding compound of the formula I. Suitable temperatures for the hydrolysis are those between about 0° and 120° C., temperatures between about 60° and 100° C. being preferred. The reaction can be carried out with or without water-miscible co-solvents. Suitable solvents include alcohols, such as methanol, ethanol, 2-propanol or 1,2-ethanediol, or ethers, such as 1,4-dioxane or tetrahydrofuran.

The 2-amino-thiophenol starting compounds of the formula II can be prepared by methods analogous to those described in the literature. Thus, for example, 4-fluoro-2-mercapto-aniline (m.p. 139°–141° C.) can be obtained by hydrolysis of 6-fluoro-2-benzothiazole-amine with boiling aqueous potassium hydroxide solution, which procedure is analogous to that described in R. L. Mital and S. K. Jain, J. Chem. Soc. (C) 1969, 2148; or S. K. Jain and R. L. Mital, Z. Naturforsch. 32B, 821 (1977); or H. Hauser, Helv. Chim. Acta 11, 208 (1928); or R. Schuloff et al., Ber.Dtsch. Chem. Ges. 61, 2541 (1928).

The starting compounds of the formula III wherein X is chlorine or bromine can be prepared from corresponding 2-benzothiazole-amines by reaction with a warm concentrated hydrohalic acid and sodium nitrite [See H. Mazzone and G. Pappalardo, Il Farmaco, Ed. Sc. 32, 348–354 (1977)]. Thus, for example, 2,6-dichlorobenzothiazole (m.p. 99°–101° C.) can be obtained from 6-chloro-2-benzothiazole-amine, and 2-chloro-6-fluorobenzothiazole (m.p. 92°–93° C.) can be obtained from 6-fluoro-2-benzothiazole-amine.

The starting compounds of the formula III wherein X is alkoxy can be obtained from the corresponding N-arylthiourethanes by reaction with a hot aqueous-alcoholic solution of potassium hexacyanoferrate-(III) and sodium hydroxide [see R. F. Hunter and E. R. Parken, J. Chem. Soc. 1935, 1755–1761]. In this way the following compounds are prepared, for example:

7-Chloro-2-ethoxy-benzothiazole (an oil, which can be used in the next step without complete purification), as well as 5-chloro-2-ethoxy-benzothiazole, m.p. 74°–75° C. (petroleum ether) from (3-chlorophenyl)-thiocarbamic acid 0-ethyl ester, m.p. 78°–79° C. (methanol/water);

6-Chloro-2-ethoxybenzothiazole, m.p. 60°–61° C. (ethanol), from (4-chlorophenyl)-thiocarbamic acid 0-ethyl ester, M.p. 103°–105° C. (ethanol);

5,6-Dimethoxy-2-ethoxy-benzothiazole (82% of theory; which can be used without purification in the next step) from (3,4-dimethoxyphenyl)-thiocarbamic acid 0-ethyl ester; and 2-Ethoxy-4-methyl-benzothiazole (31% of theory; non-crystallizing oil) from (2-methyl-phenyl)-thiocarbamic acid 0-ethyl ester, m.p. 37° C. (petroleum ether).

The necessary N-aryl-thiourethanes are obtained from N-aryl-isothiocyanates with anhydrous ethanol in the presence of quinoline (R. F. Hunter and E. R. Parken, J. Chem. Soc. 1935, 1755–1761).

The o-nitrophenyl-thio-acetic acid starting compounds of the formula IV are prepared, for example, from corresponding o-halo-nitrobenzenes and thioglycolic acid, either in boiling aqueous-alcoholic sodium hydroxide solution [analogous to A. F. Aboulezz, S. M. A. Zayed, W. S. El-Hamouly and M. I. El-Sheikh, Egypt. J. Chem. 16, 355–359 (1973)] or preferably in anhydrous dimethyl sulfoxide and in the presence of sodium methylate. Thus, the following compounds can be obtained in this manner:

(a) from 4-Chloro-3-nitro-anisole: [(4-Methoxy-2-nitrophenyl)-thio]acetic acid, m.p. 173°–174° C. (methanol);

(b) from 2,3-Dichloro-nitrobenzene: [(2-Chloro-6-nitrophenyl)-thio]acetic acid, m.p. 110°–112° C. (methanol);

(c) from 2-Chloro-4,5-dimethoxy-nitrobenzene: [(4,5-Dimethoxy-2-nitrophenyl)-thio]acetic acid, m.p. 217° C. (methanol); and (d) from 2-Chloro-4-methyl-nitrobenzene: [(4-methyl-2-nitrophenyl)-thio]acetic acid, m.p. 186°–187° C. (from ethanol).

The following examples illustrate the present invention and will enable others skilled in the art to understand it more completely. It should be understood, however, that the invention is not limited solely to the particular examples given below.

EXAMPLE 1

6-Fluoro-2(3H)-benzothiazolone 300.0 gm (1.87 mol) of N,N'-carbonyl-diimidazole were added in portions to a solution of 194.5 gm (1.75 mol) of 4-fluoro-2-mercapto-aniline in 2.5 liters of anhydrous tetrahydrofuran while stirring and maintaining the temperature between 45° and 50° C. The mixture was subsequently refluxed for 30 minutes, and 1.7 liters of solvent were distilled from the solution. The remaining solution was filtered while still hot, and stirred into 3 liters of water. After 30 minutes the precipitated product was collected by suction filtration and washed thoroughly with water. By recrystallization from ethanol and from 1,2-dichloroethane, each time in the presence of activated charcoal, 95.3 gm (43% of theory) of colorless crystals with a melting point of 188°–189° C. were obtained.

$C_7H_4FNOS$ (169.17)— Calc.: C-49.70%; H-2.38%; N-8.28%; S-18.95%. Found: C-49.55%; H-2.46%; N-8.45%; S-19.00%.

EXAMPLE 2

5-Methoxy-2(3H)-benzothiazolone (a) 3-Acetyl-5-methoxy-2(3H)-benzothiazolone

A solution of 24.5 gm (0.1007 mol) of [(4-methoxy-2-nitro-phenyl)-thio]acetic acid in 150 ml of acetic acid anhydride was refluxed for 6 hours. Excess acetic acid anhydride was then distilled off in an aspirator vacuum, and the residue was taken up in a mixture of water and dichloromethane. The methylene chloride phase was evaporated. The residue was purified chromatographically on silica gel, using dichloromethane/ethyl acetate (volume ratio of 1:1) for elution, and finally recrystallized from diisopropyl ether/ethyl acetate (1:1) in the presence of activated charcoal. 10.4 gm (46% of theory) of colorless crystals with a melting point of 112°–113° C. were obtained.

$C_{10}H_9NO_3S$ (223.25)— Calc.: C-53.80%; H-4.06%; N-6.27%; S-14.36%. Found: C-53.84%; H-4.26%; N-6.31%; S-14.60%.

(b) 5-Methoxy-2(3H)-benzothiazolone 7.0 gm (0.0314 mol) of 3-acetyl-5-methoxy-2(3H)-benzothiazolone were suspended in a mixture of 210 ml of 5 N hydrochloric acid and 70 ml of ethanol, and the suspension was refluxed for one hour. The still hot mixture was filtered, diluted with 200 ml of water and brought to a temperature of 5° C. by external cooling with ice. After standing for 2 hours, the precipitate was filtered off, and the dried product was purified chromatographically on silica gel, using 1,2-dichloroethane-acetone (volume ratio 9:1) for elution, and finally recrystallized from methanol and from 1,2-dichloroethane, each time in the presence of activated charcoal. The slightly yellow crystals obtained with a yield of 3.25 gm (57% of theory) melted at 168°–170° C.

$C_8H_7NO_2S$ (181.21)— Calc.: C-53.03%; H-3.89%; N-7.73%; S-17.69%. Found: C-53.20%; H-3.90%; N-7.74%; S-17.70%.

EXAMPLE 3

7-Chloro-2(3H)-benzothiazolone (a) 3-Acetyl-7-chloro-2(3H)-benzothiazolone

A mixture of 79.0 gm (0.32 mol) of [(2-chloro-6-nitrophenyl)-thio]acetic acid, 150.0 gm (1.83 mol) of anhydrous sodium acetate and 600 ml of acetic acid anhydride was heated for 30 minutes at 100° C. The acetic acid anhydride was distilled off in an aspirator vacuum, the residue was stirred with 1 liter of water, and the precipitate was collected by suction filtration. After purification by chromatography on silica gel, using dichloromethane/ethyl acetate (volume ratio 1:1) for elution, the product was recrystallized from ethanol. 19.2 gm (26% of theory) of colorless crystals with a melting point of 74° C. were obtained.

(b) 7-Chloro-2(3H)-benzothiazolone

Prepared analogous to Example 2(b) from 3-acetyl-7-chloro-2(3H)-benzothiazolone with a yield of 90% of theory. M.p. 202°–203° C. (1,2-dichloro-ethane).

$C_7H_4ClNOS$ (185.63)— Calc.: C-45.29%; H-2.17%; Cl-19.10%; N-7.55%; S-17.27%. Found: C-45.24%; H-2.26%; Cl-19.40%; N-7.64%; S-17.20%.

EXAMPLE 4

5,6-Dimethoxy-2(3H)-benzothiazolone (a) 3-Acetyl-5,6-dimethoxy-2(3H)-benzothiazolone Prepared analogous to Example 2(a) from [(4,5-dimethoxy-2-nitrophenyl)-thio]acetic acid and acetic acid anhydride with a yield of 34% of theory. M.p.: 164°–165° C. (diisopropyl ether/ethyl acetate).

(b) 5,6-Dimethoxy-2(3H)-benzothiazolone 2.533 gm (0.01 mol) of 3-acetyl-5,6-dimethoxy-2(3H)-benzothiazolone were refluxed for 2 hours in a mixture of 40 ml of ethanol and 50 ml of concentrated ammonia. The mixture was concentrated to one-fourth of its original volume, allowed to cool and filtered. The dried residue was purified by chromatography on silica gel, using 1,2-dichloroethane/acetone (volume ratio 9:1) for elution. The residues of the evaporated eluates were recrystallized from methanol in the presence of activated charcoal, yielding 1.78 gm (84% of theory) of the desired product having a melting point of 192°–193° C.

$C_9H_9NO_3S$ (211.25)— Calc.: C-51.17%; N-4.29%; N-6.63%; S-15.18%. Found: C-51.57%; H-4.42%; N-6.86%; S-15.22%.

EXAMPLE 5

5,6-Dimethoxy-2(3H)-benzothiazolone 19.7 gm (82 mmols) of 5,6-dimethoxy-2-ethoxybenzothiazole were dissolved in 500 ml of ethanol and admixed dropwise at the boiling point with 64 ml of concentrated aqueous hydrochloric acid. After refluxing the mixture for 3 hours, the solvent was evaporated. The residue was recrystallized from methanol. 8.1 gm (48% of theory) of 5,6-dimethoxy-2(3H)-benzothiazolone having a melting point of 191° C. were obtained.

$C_9H_9NO_3S$ (211.25)— Calc.: C-51.17%; H-4.29%; N-6.63%; S-15.18%. Found: C-51.20%; H-4.24%; N-6.53%; S-15.40%.

EXAMPLE 6

6-Chloro-2(3H)-benzothiazolone

Prepared analogous to Example 5 from 6-chloro-2-ethoxy-benzothiazole and concentrated hydrochloric acid with a yield of 56% of theory. M.p.: 212°–213° C. (toluene)

$C_7H_4ClNOS$ (185.63)— Calc.: C-45.29%; H-2.17%; Cl-19.10%; N-7.55%; S-17.27%. Found: C-45.40%; H-2.23%; Cl-19.00%; N-7.63%; S-17.36%.

EXAMPLE 7

7-Chloro-2(3H)-benzothiazolone (a) O-Ethyl (3-Chlorophenyl)-thiocarbamate

A mixture of 45.5 gm (0.268 mol) of 3-chlorophenylisothiocyanate, 200 ml of anhydrous ethanol and 1 ml of quinoline was refluxed for 48 hours. Then, the reaction mixture was evaporated in an aspirator vacuum, the residue was taken up in ether, and the resulting solution was washed first with 5% hydrochloric acid and then thoroughly with water, dried, and evaporated again. After recrystallization from methanol/water, 49.5 gm (86% of theory) of colorless crystals with a melting point of 78°–79° C. were obtained.

(b) 7-Chloro-2-ethoxy-benzothiazole 20 ml-portions of a mixture of 49.5 gm (0.24 mol) of O-ethyl (3-chlorophenyl)-thiocarbamate, 60 ml of ethanol, 350 ml of an aqueous 30% sodium hydroxide solution, and 300 ml of water were added at intervals of 5 minutes to a solution of 494 gm (1.5 mol) of potassium hexacyanoferrate (III) in 600 ml of water at 80°–90° C. After heating the mixture for 2 hours at 90° C., 200 gm (0.61 mol) of potassium hexacyanoferrate (III) were added again, and the mixture was heated for another 3 hours at 90° C. After cooling, the mixture was diluted with 3 liters of water, extracted exhaustively with ether, and the separated organic phase was washed with water and dried over sodium sulfate. The residue remaining after evaporation of the solvent was purified by chromatography on 500 gm of silica gel, using dichloromethane/petroleum ether (volume ratio of 1:1) for elution. The fractions containing the two principal products were combined and evaporated. The residual crystal sludge yielded, after two successive recrystallizations from petroleum ether, 7.5 gm of colorless crystals having a melting point of 74°–75° C., which consisted according to spectroscopic examination of 5-chloro-2-ethoxy-benzothiazole. For the purpose of isolating the desired 7-chloro-2-ethoxybenzothiazole, i.e. the substance with the lower $R_f$ value, the combined mother liquors were chromatographed on 500 gm of silica gel, using petroleum ether/dichloromethane as the eluant. The 7-chloro-2-ethoxy-benzothiazole, a light yellow oil obtained after evaporation of the corresponding eluates, was used in the next step without further purification. Yield: 15.5 gm (32% of theory).

(c) 7-Chloro-2(3H)-benzothiazolone

Prepared analogous to Example 5 from 7-chloro-2-ethoxy-benzothiazole and concentrated hydrochloric acid with a yield of 38% of theory. M.p.: 202°–203° C. (after recrystallization from methanol and from diisopropyl ether).

$C_7H_4ClNOS$ (185.63)— Calc.: C-45.29%; H-2.17%; Cl-19.10%; S-17.27%. Found: C-45.15%; H-2.19%; Cl-19.23%; S-17.43%.

EXAMPLE 8

6-Chloro-2(3H)-benzothiazolone 4.081 gm (0.02 mol) of 2,6-dichloro-benzothiazole were refluxed for 4 hours in 100 ml of a mixture of equal parts of ethanol and concentrated hydrochloric acid. After distilling the reaction mixture with 100 ml of water, the resulting precipitate was filtered off and washed thoroughly with water. For further purification the precipitate was taken up in aqueous 10% sodium hydroxide, the solution was filtered, and the filtrate was extracted twice with 100 ml each of ether. The aqueous phase was acidified with hydrochloric acid, and the resulting precipitate was collected by suction filtration, washed with water and recrystallized once from ethanol and once from toluene, each time in the presence of activated charcoal. 3.1 gm (83% of theory) of crystals with a melting point of 212°–213° C. were obtained.

According to mixed melting point determination, elemental analysis, and thin-layer chromatography, the product was identical to the product obtained in Example 6.

EXAMPLE 9

6-Fluoro-2(3H)-benzothiazolone

Prepared analogous to Example 8 from 2-chloro-6-fluoro-benzothiazole and concentrated hydrochloric acid with a yield of 45% of theory. M.p.: 189°–190° C. (1,2-dichloro-ethane).

According to mixed melting point determination, elemental analysis and IR-spectrum, the product was identical to the product obtained in Example 1.

EXAMPLE 10

4-Methyl-2(3H)benzothiazolone

Prepared analogous to Example 5 from 2-ethoxy-4-methyl-benzothiazole and concentrated hydrochloric acid with a yield of 81% of theory. M.p.: 207°–208° C. (xylene/gasoline 1:1)

$C_8H_7NOS$ (165.21)— Calc.: C-58.16%; H-4.27%; N-8.48%; S-19.41%. Found: C-57.42%; H-4.24%; N-8.50%; S-19.45%.

EXAMPLE 11

4-Chloro-benzothiazol-2(3H)-one

Prepared analogous to Example 5 from 4-chloro-2-methoxy-benzothiazole and concentrated hydrochloric acid with a yield of 26% of theory. M.p.: 205°–206° C. (from 1,2-dichloro-ethane)

$C_7H_4ClNOS$ (185.63)— Calc.: C-45.29%; H-2.17%; Cl-19.10%; N-7.55%; S-17.27%. Found: C-45.29%; H-2.04%; Cl-20.00%; N-7.60%; S-17.08%.

EXAMPLE 12

5-Methyl-benzothiazol-2(3H)-one

Analogous to Example 2(a), 2-acetyl-5-methyl-2-(3H)-benzothiazolone, m.p. 86°–88° C. (from isooctane/diisopropyl ether), was prepared with a yield of 51% of theory, starting from [(4-methyl-2-nitrophenyl)-thio]-acetic acid. This intermediate was subsequently treated with 5 N hydrochloric acid analogous to Example 2(b). 5-Methyl-2(3H)-benzothiazolone was obtained with a yield of 74% of theory; m.p. 178°–180° C. (from ethanol/water 1:1).

$C_8H_7NOS$ (165.21)— Calc.: C-58.16%; H-4.27%; N-8.48%; S-19.41%. Found: C-57.97%; H-4.36%; N-8.66%; S-19.65%.

The analgesic and antipyretic activities, as well as the acute toxicities of the compounds of the formula I in warm-blooded animals, such as rats and mice, were ascertained by the methods described below, where A=5-methoxy-benzothiazol-2(3H)-one,
B=6-fluoro-benzothiazol-2(3H)-one,
C=7-chloro-benzothiazol-2(3H)-one,
D=6-chloro-benzothiazol-2(3H)-one,
E=5,6-dimethoxy-benzothiazol-2(3H)-one,
F=4-methyl-benzothiazol-2(3H)-one,
G=5-methyl-benzothiazol-2(3H)-one, and
H=4-chloro-benzothiazol-2(3H)-one.

The compounds were tested for their analgesic effect on the inflammation pain of the rat, their analgesic effect on the heat pain of the mouse, their temperature-reducing effect in the rat, and their acute toxicity in the mouse.

METHODOLOGY

1. Effect on the Inflammation Pain of the Rat

The test arrangement corresponded to that indicated by RANDALL-SELITTO [Arch. Int. Pharmacodyn. 111, 409 (1957)]. Male Chbb:THOM-rats having body weights of from 100 to 130 grams received a subplantar injection of 0.1 ml of a 5% suspension of yeast cells in 5.55% glucose solution in a rear paw. At $1\frac{1}{2}$ and $2\frac{1}{4}$ hours, respectively, after injection of the phlogistic, the animals received various doses of the test substance as a trituration in 1% methyl cellulose (1 ml/100 g of animal) through an esophageal tube. Control animals received corresponding volumes of the vehicle.

Ninety and forty-five minutes, respectively, after application of the test substance (that is, three hours after the subplantar injection of the yeast suspension), the threshold pain was determined in the rat in terms of the milligrams of bearing pressure on a paw, based on the weight of the animals.

From the pain threshold, measured according to the different doses of the test substance, and with the linear regression analysis according to LINDER [Statistische Methoden, 4th ed., pp. 148-162, Birkhäuser, Basel, 1964], and $ED_{50}$ dose with the confidence limits according to FIELLER [Quart. J. Pharm. Pharmacol., 17, 117 (1944)] was determined. The $ED_{50}$ dose is one in which the pain threshold rises by 50%, as compared to the controls. The results are set forth in the following tables:

TABLE 1

After Forty-five Minutes

| Test compound | $ED_{50}$ (mg/kg) | Confidence limits at 95% probability (mg/kg) |
|---|---|---|
| A | 90 | (84-95) |
| B | 121 | (114-129) |
| C | 106 | (99-113) |
| D | 175 | (153-208) |
| E | 43 | (40-45) |
| F | 174 | (162-186) |
| G | 103 | (97-111) |
| H | 24 | (21-27) |

TABLE 2

After Ninety Minutes

| Test compound | $ED_{50}$ (mg/kg) | Confidence limits at 95% probability (mg/kg) |
|---|---|---|
| A | 150 | (142-157) |
| B | 76 | (71-80) |
| C | 105 | (92-120) |
| D | 129 | (122-138) |
| E | 40 | (38-42) |
| F | 202 | (187-217) |
| G | 97 | (89-106) |
| H | 23 | (20-25) |

2. Effect on the Heat Sensitivity of the Mouse

The test performed according to a modification of the method described by CHEN and BECKMAN [Science, 113, 631 (1951)] in male Chbb:NMRI (SPF)-mice with an average weight of 20 grams. The "hot plate" consisted of aluminium and had a temperature of 52° C. on its surface.

The test substances were administered as trituration in 1% methyl cellulose (0.1 ml/10 gm of mouse) by means of an esophageal tube. Before treatment with the test substance, the animals were twice put on the hot plate at an interval of 30 minutes, whereby their individual times of reaction were measured. After treatment with a test substance, the times of reaction of the animals were again measured in an interval of 30 minutes.

From the average maximum increase of the time of reaction obtained after treatment with different doses, and after linear regression analysis according to LINDER, an $ED_{100}$ dose with the confidence limits according to FIELLER was calculated. The $ED_{100}$ dose is one which increased the time of reaction by 100%. The results of the testing are set forth in the following table:

TABLE 3

| Test compound | $ED_{100}$ (mg/kg) | Confidence limits in 95% probability (mg/kg) |
|---|---|---|
| A | 218 | (127-259) |
| B | 165 | (140-261) |
| E | 92 | (62-127) |
| F | 113 | (100-124) |
| G | 178 | — |
| H | 125 | — |

3. Effect on the Body Temperature of the Rat

The temperature-lowering activity, i.e. antipyretic activity, was tested by the observation of the temperature curve given by rectally measured body temperatures of partially immobilized Chbb:THOM-rats having body weights of between 125 and 150 grams. The body temperatures were measured by thermocouples inserted into rectums. The test substances were administered as a trituration in a 1% methyl cellulose in portions of 1.0 ml/100 gm of animal using an esophageal tube.

From the values for the average maximum decline of temperature, which were gained after the administration of the different doses of the test substance, and after a linear regression analysis according to LINDER, an $ED_{-1.5° C.}$ was calculated with the confidence limits according to FIELLER as the dose which decreases the body temperature by 1.5° C. The results of the testing are set forth in the following table:

TABLE 4

| Test compound | $ED_{-1.5° C.}$ (mg/kg) | Confidence limits at 95% probability (mg/kg) |
|---|---|---|
| A | 58 | (48-77) |
| B | 83 | (71-100) |
| D | 103 | (80-142) |
| E | 29 | (25-33) |
| F | 118 | (80-157) |
| G | 37 | (32-42) |
| H | 16 | (13-18) |

4. Acute Toxicity in Mice

The acute toxicity was determined in Chbb:NMRI (SPF)-mice of both sexes, having an average body weight of 20 gm. The test compounds were administered as a trituration in 1% methyl cellulose (0.5 ml/10 gm of animal) by means of an esophageal tube. The calculation of the $LD_{50}$ values was effected according to the method of LITCHFIELD and WILCOXON [J. Pharmacol. Exp. Ther. 96, 99 (1949)], based on the percentage of animals which died within 14 days after administration of different doses. The results of the testing are set forth in the following table.

TABLE 5

| Test compound | LD$_{50}$ (mg/kg) | Confidence limits at 95% probability (mg/kg) |
|---|---|---|
| A | 1600 | (1310–1950) |
| B | 1650 | (1320–2062) |
| C | 10000* | |
| F | 8000** | |
| G | 2650 | (2240–3140) |

*after administration of this dose all 10 animals survived;
**after administration of this dose 4 out of 20 animals died.

The tested compounds, i.e. compounds A through G, were characterized by very low toxicity and good analgesic and antipyretic properties.

For pharmaceutical purposes the compounds of the formula I are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds of the formula I is from 0.3 to 9 mgm/kg, preferably 0.7 to 4.5 mgm/kg, and the daily dose rate is 0.9 to 26 mgm/kg, preferably 2.6 to 13 mgm/kg.

The following examples illustrate a few pharmaceutical dosage unit compositions comprising a compound of the formula I as an active ingredient and represent the best modes contemplated of using the invention. The parts are parts by weight unless otherwise specified.

EXAMPLE 13

Tablets

The tablet composition is compounded from the following ingredients:

| | |
|---|---|
| 5-Methoxy-benzothiazol-2(3H)-one | 50.0 parts |
| Lactose | 128.0 parts |
| Potato starch | 40.0 parts |
| Magnesium stearate | 2.0 parts |
| Total | 220.0 parts |

Preparation

An aqueous 10% slurry is prepared from some of the potato starch by heating it. The active ingredient, the lactose and the remainder of the potato starch are intimately admixed with each other, the mixture is moistened with the potato starch slurry, and the moist mass is granulated by passing it through a 1.5 mm-mesh screen. The granulate is dried at 45° C., again passed through the screen, admixed with the magnesium stearate, and the resulting composition is compressed into 220 mgm-tablets. Each tablet is an oral dosage unit composition containing 50 mgm of the active ingredient.

EXAMPLE 14

Coated tablets

The tablets prepared in Example 13 are coated with a thin shell consisting essentially of a mixture of sugar and talcum, and the coated tablets are polished with beeswax.

EXAMPLE 15

Gelatin capsules

5-Methoxy-benzothiazole-2(3H)-one is micronized, and 60 mgm-portions thereof are filled into gelatin capsules of suitable size.

EXAMPLE 16

Suppositories

The suppository composition is compounded from the following ingredients:

| | |
|---|---|
| 5-Methoxy-benzothiazole-2(3H)-one | 60.0 parts |
| Suppository base (e.g. cocoa butter) | 1640.0 parts |
| Total | 1700.0 parts |

Preparation

The pulverized active ingredient is homogeneously blended into the suppository base which has previously been melted and cooled to 40° C. The composition is cooled to 37° C., and 1700 mgm-portions thereof are poured into cooled suppository molds and allowed to harden therein. Each suppository is a rectal dosage unit composition containing 60 mgm of the active ingredient.

EXAMPLE 17

Suspension

The suspension is compounded from the following ingredients:

| | |
|---|---|
| 5-Methoxy-benzothiazole-2(3H)-one | 4.0 parts |
| Carboxymethyl cellulose | 0.1 parts |
| Methyl p-hydroxy-benzoate | 0.05 parts |
| Propyl p-hydroxy-benzoate | 0.01 parts |
| Cane sugar | 10.0 parts |
| Glycerin | 5.0 parts |
| Sorbitol solution, 70% | 20.0 parts |
| Flavoring | 0.3 parts |
| Distilled water | 100.0 parts by vol. |

Preparation

The distilled water is heated to 70° C., and the p-hydroxy-benzoates, the glycerin and the carboxymethyl cellulose are dissolved therein while stirring. The solution is cooled to room temperature, and the active ingredient is uniformly dispersed therein by stirring. The sugar, the sorbitol solution and the flavoring are then added to and dissolved in the suspension, and the composition is de-aerated in vacuo while stirring. 5 ml of the suspension are an oral dosage unit composition containing 200 mgm of the active ingredient.

Any one of the other compounds of the formula I may be substituted for the particular active ingredient in Examples 13 to 17. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of relieving pain or reducing fever in a warm-blooded animal in need thereof, which comprises perorally, parenterally or rectally administering to said animal an effective analgesic or antipyretic amount of a compound of the formula

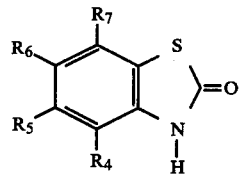

wherein $R_5$ is methyl or methoxy, and $R_4$, $R_6$ and $R_7$ are hydrogen; or $R_6$ is fluorine or chlorine, and $R_4$, $R_5$ and $R_7$ are hydrogen; or $R_7$ is chlorine, and $R_4$, $R_5$ and $R_6$ are hydrogen; or $R_5$ and $R_6$ are methoxy, and $R_4$ and $R_7$ are hydrogen; or $R_4$ is methyl or chlorine, and $R_5$, $R_6$ and $R_7$ are hydrogen.

2. The method of claim 1, where $R_5$ is methyl or methoxy, and $R_4$, $R_6$ and $R_7$ are hydrogen; or $R_7$ is chlorine, and $R_4$, $R_5$ and $R_6$ are hydrogen; or $R_5$ and $R_6$ are methoxy, and $R_4$ and $R_7$ are hydrogen; or $R_4$ is methyl or chlorine, and $R_5$, $R_6$ and $R_7$ are hydrogen.

3. The method of claim 1, where said compound is 5-methoxy-benzothiazol-2(3H)-one.

4. The method of claim 1, where said compound is 4-methyl-benzothiazol-2(3H)-one.

* * * * *